US00PP27860P3

(12) United States Plant Patent
Grazzini

(10) Patent No.: US PP27,860 P3
(45) Date of Patent: Apr. 4, 2017

(54) *SALVIA* PLANT NAMED 'G13592'

(50) Latin Name: *Salvia farinacea*
Varietal Denomination: G13592

(71) Applicant: Richard A. Grazzini, Bellefonte, PA (US)

(72) Inventor: Richard A. Grazzini, Bellefonte, PA (US)

(73) Assignee: GardenGenetics LLC, Bellefonte, PA (US)

( * ) Notice: Subject to any disclaimer, the term of this patent is extended or adjusted under 35 U.S.C. 154(b) by 74 days.

(21) Appl. No.: 14/545,631

(22) Filed: May 29, 2015

(65) Prior Publication Data

US 2016/0353649 P1 Dec. 1, 2016

(51) Int. Cl.
*A01H 5/02* (2006.01)

(52) U.S. Cl.
USPC ..... Plt./475

(58) Field of Classification Search
USPC ..... Plt./475
See application file for complete search history.

*Primary Examiner* — June Hwu
(74) *Attorney, Agent, or Firm* — C. A. Whealy

(57) ABSTRACT

A new and distinct cultivar of *Salvia* plant named 'G13592', characterized by its upright to somewhat outwardly spreading plant habit; vigorous growth habit; relatively large dark green-colored leaves; freely and continuous flowering habit; relatively large inflorescences with relatively large dark blue-colored flowers; and good garden performance.

1 Drawing Sheet

Botanical designation: *Salvia farinacea.*
Cultivar denomination: 'G13592'.

BACKGROUND OF THE INVENTION

The present invention relates to a new and distinct cultivar of *Salvia* plant, botanically known as *Salvia farinacea* and hereinafter referred to by the name 'G13592'.

The new *Salvia* plant is a product of a planned breeding program conducted by the Inventor in Bellefonte, Pa. The objective of the breeding program is to create new vigorous *Salvia* plants with large flowers, long flowering period and good garden performance.

The new *Salvia* plant originated from an open-pollination in August, 2010 of a proprietary selection of *Salvia farinacea* identified as code number 13721, not patented, as the female, or seed, parent with an unknown selection of *Salvia farinacea*, as the male, or pollen, parent. The new *Salvia* plant was discovered and selected by the Inventor as a single flowering plant from within the progeny of the stated open-pollination in a controlled outdoor nursery environment in Bellefonte, Pa. on May 15, 2011.

Asexual reproduction of the new cultivar by vegetative terminal cuttings in Bellefonte, Pa., since Oct. 21, 2011 has shown that the unique features of this new *Salvia* plant are stable and reproduced true to type in successive generations.

SUMMARY OF THE INVENTION

Plants of the new *Salvia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'G13592'.

These characteristics in combination distinguish 'G13592' as a new and distinct *Salvia* plant:

1. Upright to somewhat outwardly spreading plant habit.
2. Vigorous growth habit.
3. Relatively large dark green-colored leaves.
4. Freely and continuous flowering habit.
5. Relatively large inflorescences with relatively large dark blue-colored flowers.
6. Good garden performance.

Plants of the new *Salvia* can be compared to plants of the female parent selection. Plants of the new *Salvia* differ from plants of the female parent selection in the following characteristics:

1. Plants of the new *Salvia* are more vigorous than plants of the female parent selection.
2. Leaves of plants of the new *Salvia* are darker green in color than leaves of plants of the female parent selection.
3. Inflorescences of plants of the new *Salvia* are longer than inflorescences of plants of the female parent selection.
4. Flowers of plants of the new *Salvia* are darker blue in color than flowers of plants of the female parent selection.

Plants of the new *Salvia* can be compared to plants of *Salvia farinacea* 'Victoria Blue', not patented. In side-by-side comparisons conducted in Bellefonte, Pa., plants of the new *Salvia* differed from plants of 'Victoria Blue' in the following characteristics:

1. Plants of the new *Salvia* were more uniform in growth habit than plants of 'Victoria Blue'.
2. Plants of the new *Salvia* were more vigorous than plants of 'Victoria Blue'.
3. Inflorescences of plants of the new *Salvia* were longer than inflorescences of plants of 'Victoria Blue'.

4. Flowers of plants of the new *Salvia* were larger and darker blue in color than flowers of plants of 'Victoria Blue'.
5. Plants of the new *Salvia* flowered for a longer period of time than plants of 'Victoria Blue'.

Plants of the new *Salvia* can also be compared to plants of *Salvia farinacea* 'Salv Bule', disclosed in U.S. Plant Pat. No. 20,625. In side-by-side comparisons conducted in Bellefonte, Pa., plants of the new *Salvia* differed from plants of 'Salv Bule' in the following characteristics:

1. Plants of the new *Salvia* were more vigorous than plants of 'Salv Bule'.
2. Plants of the new *Salvia* were more outwardly spreading than and not as upright as plants of 'Salv Bule'.
3. Plants of the new *Salvia* flowered later than plants of 'Salv Bule'.
4. Flowers of plants of the new *Salvia* were larger than flowers of plants of 'Salv Bule'.
5. Plants of the new *Salvia* and 'Salv Bule' differed in flower color as plants of 'Salv Bule' had violet blue-colored flowers.

BRIEF DESCRIPTION OF THE PHOTOGRAPHS

The accompanying colored photographs illustrate the overall appearance of the new *Salvia* plant showing the colors as true as it is reasonably possible to obtain in colored reproductions of this type. Colors in the photographs may differ slightly from the color values cited in the detailed botanical description which accurately describe the actual colors of the new *Salvia* plant.

The photograph on the right side of the sheet is a side perspective view of a typical flowering plant of 'G13592' grown in a container.

The photograph on the left side of the sheet is a close-up view of a typical flowering plant of 'G13592' grown in a container.

DETAILED BOTANICAL DESCRIPTION

The aforementioned photographs and following observations, measurements and values describe plants grown during the early spring in 11.5-cm containers in a polycarbonate-covered greenhouse in Bellefonte, Pa. and under cultural practices which closely approximate commercial production. During the production of the plants, day temperatures ranged from 18° C. to 24° C. and night temperatures ranged from 13° C. to 16° C. Plants were pinched one time and were ten weeks old when the photographs and description were taken. In the detailed description, color references are made to The Royal Horticultural Society Colour Chart, 2007 Edition, except where general terms of ordinary dictionary significance are used.

Botanical classification: *Salvia farinacea* 'G13592'.

Parentage:

*Female, or seed, parent*.—Proprietary selection of *Salvia farinacea* identified as code number 13721, not patented.

*Male, or pollen, parent*.—Unknown selection of *Salvia farinacea*, not patented.

Propagation:

*Type*.—By vegetative terminal cuttings.

*Time to initiate roots, summer*.—About 10 to 14 days at temperatures about 22° C.

*Time to initiate roots, winter*.—About 14 to 21 days at temperatures about 22° C.

*Time to produce a rooted young plant, summer*.—About 56 days at temperatures about 22° C.

*Time to produce a rooted young plant, winter*.—About 70 days at temperatures about 22° C.

*Root description*.—Medium in thickness, fibrous; white to tan in color.

*Rooting habit*.—Moderately freely branching; medium density.

Plant description:

*Plant and growth habit*.—Herbaceous perennial typically grown as a container and garden plant; upright to somewhat outwardly spreading plant habit; uniform and vigorous growth habit; flowers arranged on erect terminal racemes.

*Branching habit*.—Freely basal branching with about three to four primary lateral branches each with many axillary shoots developing per plant.

*Plant height*.—About 27.6 cm.

*Plant width*.—About 18.2 cm.

*Lateral branch description*.—Length: About 26 cm. Diameter: About 4.5 mm. Internode length: About 1.8 cm. Strength: Strong. Aspect: Mostly upright to outwardly. Texture: Pubescent, minute. Color, developing: Close to 148A to 148B. Color, developed: Close to 146A.

Leaf description:

*Arrangement*.—Opposite, simple.

*Length*.—About 6.7 cm.

*Width*.—About 4.5 cm.

*Shape*.—Ovate to elliptical.

*Apex*.—Broadly acute.

*Base*.—Obtuse.

*Margin*.—Towards the apex, broadly crenate; towards the base, mostly entire.

*Texture, upper surface*.—Smooth, glabrous.

*Texture, lower surface*.—Slightly pubescent, minute.

*Venation pattern*.—Pinnate, arcuate.

*Color*.—Developing leaves, upper surface: Close to 137C. Developing leaves, lower surface: Close to 147B. Fully expanded leaves, upper surface: Close to N137B; venation, close to 146B. Fully expanded leaves, lower surface: Close to 147B; venation, close to 147D.

*Petioles*.—Length: About 3.4 cm. Diameter: About 2 mm. Texture, upper and lower surfaces: Pubescent, minute. Color, upper surface: Close to 146B. Color, lower surface: Close to 146D.

Flower description:

*Flower arrangement and shape*.—Single bilabiate flowers arranged on erect terminal racemes; racemes conical in shape; freely flowering habit with about 146 flowers developing per inflorescence; flowers face mostly outwardly.

*Fragrance*.—None detected.

*Natural flowering season*.—Plants begin flowering about six to eight weeks after planting; long flowering period, flowering is continuous flowering from April to October in Pennsylvania.

*Flower longevity on the plant*.—Individual flowers last about five days on the plant; inflorescences last about six to ten weeks on the plant; flowers and inflorescences persistent.

*Flower buds*.—Length: About 1.3 cm. Diameter: About 5 mm. Shape: Elongated oval to oblong. Color: Close to 93B.

*Inflorescence length*.—About 5.8 cm.

*Inflorescence diameter*.—About 3.7 cm.

*Flower diameter*.—About 1.2 cm.

*Flower depth* (*height*).—About 1 cm.

*Petals*.—Arrangement: Five petals fused at the base forming a single upper banner petal (upper lip), two lateral petals and two lower petals (broad lower lip). Lobe length, banner petal: About 8 mm. Lobe length, lateral petals: About 4 mm. Lobe length, lower petals: About 1.1 cm. Lobe width, banner petal: About 4 mm. Lobe width, lateral petals: About 3 mm. Lobe width, lower petals: About 1.2 cm. Shape, all petals: Round. Apex, all petals: Round. Base, all petals: Fused into a narrow tube. Margin, all petals: Mostly entire to slightly sinuate. Texture, all petals, upper surface: Smooth, glabrous; velvety. Texture, all petals, lower surface: Densely pubescent. Color, all petals: When opening, upper surface: Close to 93A. When opening, lower surface: Close to 93C to 93D. Fully opened, upper surface: Close to 93A to 93B; color does not fade with development. Fully opened, lower surface: Close to 93C; towards the margins, close to 93A; color does not fade with development. Throat: Close to 93D and NN155B. Tube: Close to 92C to 92D.

*Calyx*.—Arrangement: Five sepals completely fused to form a campanulate calyx. Length: About 8 mm. Width: About 5 mm. Apex: Emarginate. Texture, inner surface: Smooth, glabrous. Texture, outer surface: Densely pubescent. Color, inner surface: Close to 146B to 146C. Color, outer surface: Slightly more grey than close to 97A to 97B.

*Peduncles*.—Length: About 11.5 cm. Diameter: About 4 mm. Strength: Strong. Aspect: Mostly erect. Texture: Densely pubescent. Color: Close to 187C.

*Pedicels*.—Length: About 5 mm. Diameter: Less than 1 mm. Strength: Strong. Aspect: Bending to horizontal. Texture: Pubescent, minute. Color: Close to 195C.

*Reproductive organs*.—Stamens: Quantity per flower: Two to four. Filament length: About 6 mm. Filament color: Close to 92D. Anther shape: Oval. Anther length: About 1 mm. Anther color: Close to 199B. Pollen amount: Scarce. Pollen color: Close to 162C. Pistils: Quantity per flower: One. Pistil length: About 1.8 cm. Stigma shape: Bi-parted. Stigma color: Close to 92A. Style length: About 1 cm. Style color: Close to 91D. Ovary color: Close to 151A.

*Seeds and fruits*.—Seed and fruit production has not been observed on plants of the new *Salvia*.

Disease & pest resistance: Plants of the new *Salvia* have not been noted to be resistant to pathogens and pests common to *Salvia* plants.

Garden performance: Plants of the new *Salvia* have exhibited good garden performance and to be tolerant to rain, wind and temperatures ranging from about 5° C. to about 35° C.

It is claimed:

1. A new and distinct *Salvia* plant named 'G13592' as illustrated and described.

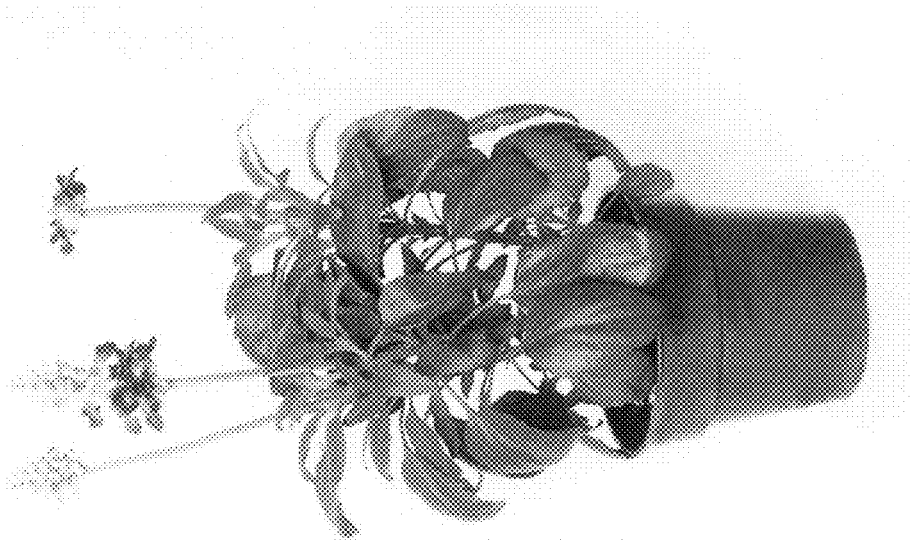
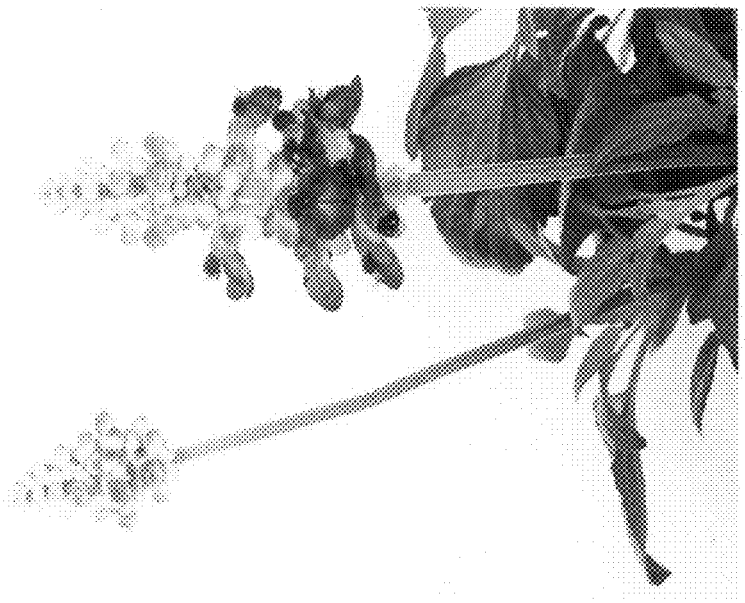

* * * * *